United States Patent [19]

Hiroshima et al.

[11] 4,247,818
[45] Jan. 27, 1981

[54] AUTOMATIC SENSITIVITY ADJUSTMENT APPARATUS FOR CALIBRATION OF A NON-DESTRUCTIVE INSPECTION INSTRUMENT

[75] Inventors: Tatsuo Hiroshima; Tetsuya Hirota, both of Amagasaki, Japan

[73] Assignee: Sumitomo Metal Industries, Inc., Osaka, Japan

[21] Appl. No.: 971,087

[22] Filed: Dec. 15, 1978

Related U.S. Application Data

[63] Continuation-in-part of Ser. No. 802,974, Jun. 2, 1977, abandoned.

[30] Foreign Application Priority Data

Jun. 18, 1976 [JP] Japan .................................. 51-072611

[51] Int. Cl.³ ...................... G01R 35/00; G01R 33/00
[52] U.S. Cl. .................................... 324/202; 324/225; 324/238; 307/264; 307/353
[58] Field of Search .................. 324/202, 225, 234–241, 324/74, 130; 307/264, 353, 355; 328/168, 173, 175; 250/214 AG; 73/1 DV, 67, 599, 618, 625

[56] References Cited

U.S. PATENT DOCUMENTS

| | | | |
|---|---|---|---|
| 3,206,689 | 9/1965 | Santana | 307/264 |
| 3,487,222 | 12/1969 | Martens | 328/173 |
| 3,714,441 | 1/1973 | Kreda | 250/214 AG |
| 3,986,037 | 10/1976 | Faulhaber | 250/214 AG |
| 4,013,961 | 3/1977 | Colebourn | 328/151 |

Primary Examiner—Gerard R. Strecker
Assistant Examiner—Walter E. Snow
Attorney, Agent, or Firm—Wenderoth, Lind & Ponack

[57] ABSTRACT

The present invention is an automatic sensitivity adjustment apparatus for calibration of a nondestructive inspection instrument with a reference standard. Calibration is performed by setting the gain of a variable gain amplifier while a reference standard containing a standard flaw is passed before the sensing means of the instrument. A discriminator circuit connected to the sensing means detects when the output of the sensing means exceeds a predeterminedlevel. A hold time controller sends a sampling enable signal to a peak hold circuit which is also connected to the sensing means to cause the peak hold circuit to sample the sensing means output. The hold time controller senses the peak in the response of the sensing means and causes the peak hold circuit to hold that peak value. The output of the peak hold circuit is applied to the input of a variable gain amplifier. A comparator compares the output of the variable gain amplifier with a reference voltage produced by a reference voltage setting means. The output of the comparator is connected to the gain control input of the variable gain amplifier in order to control the gain of the variable gain amplifier so that the output level equals the reference voltage. Switching means disables the automatic sensitivity adjustment apparatus with the gain of the variable gain amplifier thus set during the ordinary operation of the non-destructive inspection apparatus.

1 Claim, 10 Drawing Figures

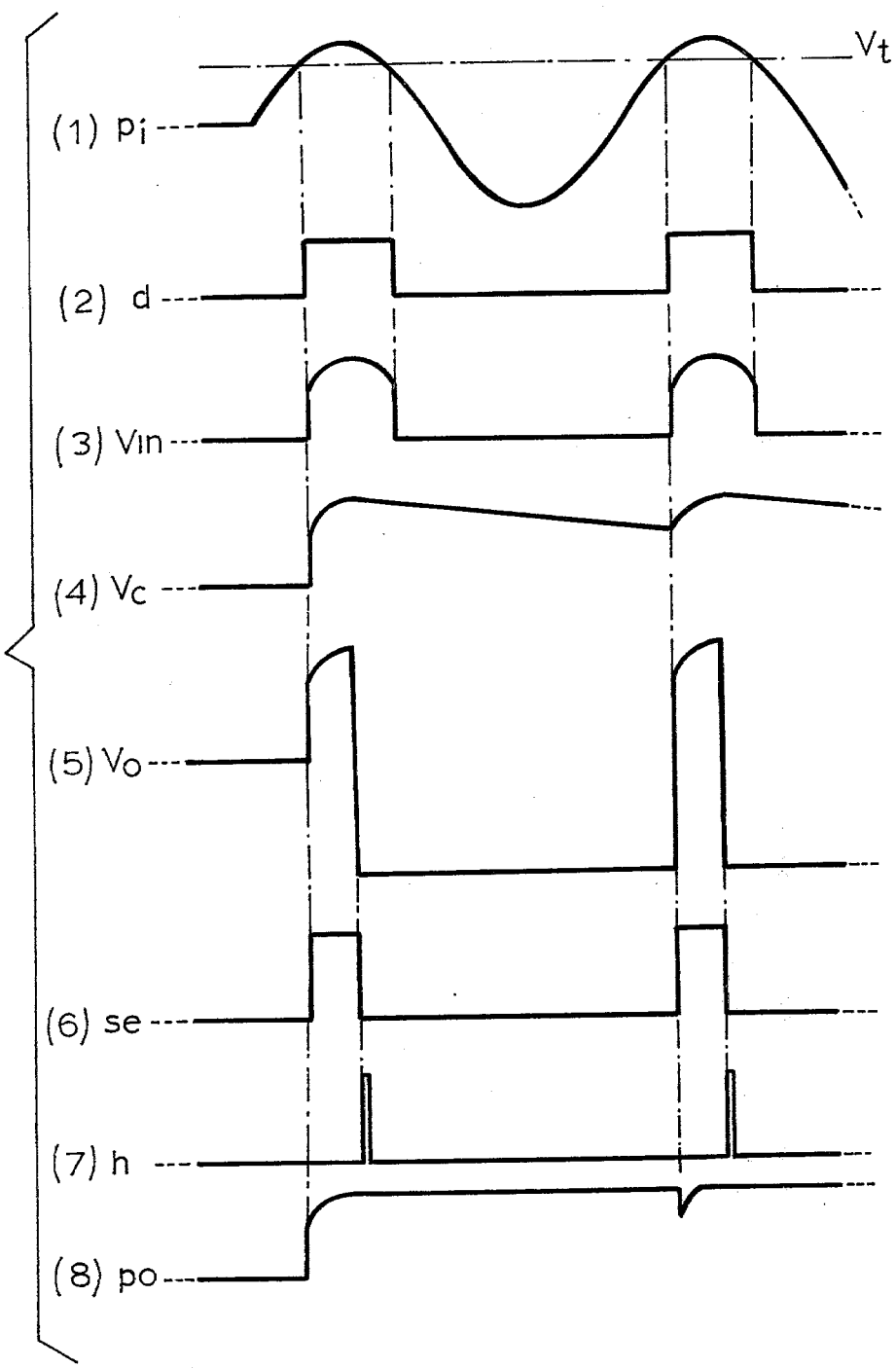

AUTOMATIC SENSITIVITY ADJUSTMENT APPARATUS FOR CALIBRATION OF A NON-DESTRUCTIVE INSPECTION INSTRUMENT

This application is a continuation-in-part of Ser. No. 802,974, filed June 2, 1977, now abandoned.

BACKGROUND OF THE INVENTION

1. Field of the Invention

This invention relates to an automatic sensitivity adjustment apparatus for use in the calibration of nondestructive inspection instruments such as ultrasonic, eddy-current and magnetic flaw detectors.

2. Description of the Prior Art

For the detection of flaws in materials such as steel rod, steel pipe or other products having a circular cross-section by means of a nondestructive inspection instruments of the above type, there is known a method in which a detecting sensor is caused to scan the surface of the work in a spiral path. For the detection of flaws in materials having a flat surface such as steel plate and billet, the sensor is driven traversely to scan the surface of the test piece in a zigzag manner. However, in order that such flaw detection may be sufficiently accurate, the nondestructive inspection instrument need be previously calibrated using a control reference standard similar to the test piece in dimensions and grade of material. This calibration has heretofore been accomplished manually by a visual monitoring of the amplitudes of pulse-waves displayed on a cathode-ray tube or a recorder, which is either built into the nondestructive inspection instrument or externally connected to the instrument. However, because in such a calibration procedure, the scanning of the sample piece by the sensor takes place under the same conditions as in actual testing, the aforesaid pulse-wave is obtainable only once per revolution in the case of spiral scanning and only twice per reciprocation in the case of zigzag scanning. This means that the signal display of the cathode-ray tube is unsatisfactory in the duration of the display and the display of the recorder is unsatisfactory in follow-up performance. Particularly where a plurality of sensors are employed, calibration is the time-consuming procedure and cannot necessarily be fully accurate.

This invention has been developed to overcome the above disadvantages and has as its object to provide an automatic sensitivity adjustment apparatus which holds the peak value of an intermittent pulse signal for a predetermined time and performs an automatic and accurate calibration of a nondestructive inspection instrument.

SUMMARY OF THE INVENTION

This invention relates to an automatic sensitivity adjustment apparatus for use in calibration of a nondestructive inspection instrument which comprises a hold control circuit disposed between a discriminator connected to a sensor of the nondestructive inspection instrument and a peak hold circuit and adapted to feed a sampling signal to the peak hold circuit and also to feed a hold signal to the peak hold circuit upon reception of an output signal from said discriminator when the signal from the sensor has attained a peak value, and a variable gain amplifier disposed at the output of the peak hold circuit, the variable gain amplifier having an output terminal which is connected to a first input terminal of a comparator and a control terminal which is connected to the output terminal of the comparator, the gain of the variable gain amplifier being automatically controlled at a value such as to make the output signal of the comparator equal to zero, the second input terminal of the comparator being connected to a reference voltage setting means to obtain a set voltage input corresponding to the optimum peak level for display of the signal from the sensor.

This invention will be described in detail by reference to the accompanying drawings.

BRIEF DESCRIPTION OF THE DRAWINGS

FIGS. 3(1)–3(8) are a series of views showing the output signal waveforms at principal stages of the circuits illustrated in FIGS. 1 and 2.

DETAILED DESCRIPTION OF THE INVENTION

Figure 1:
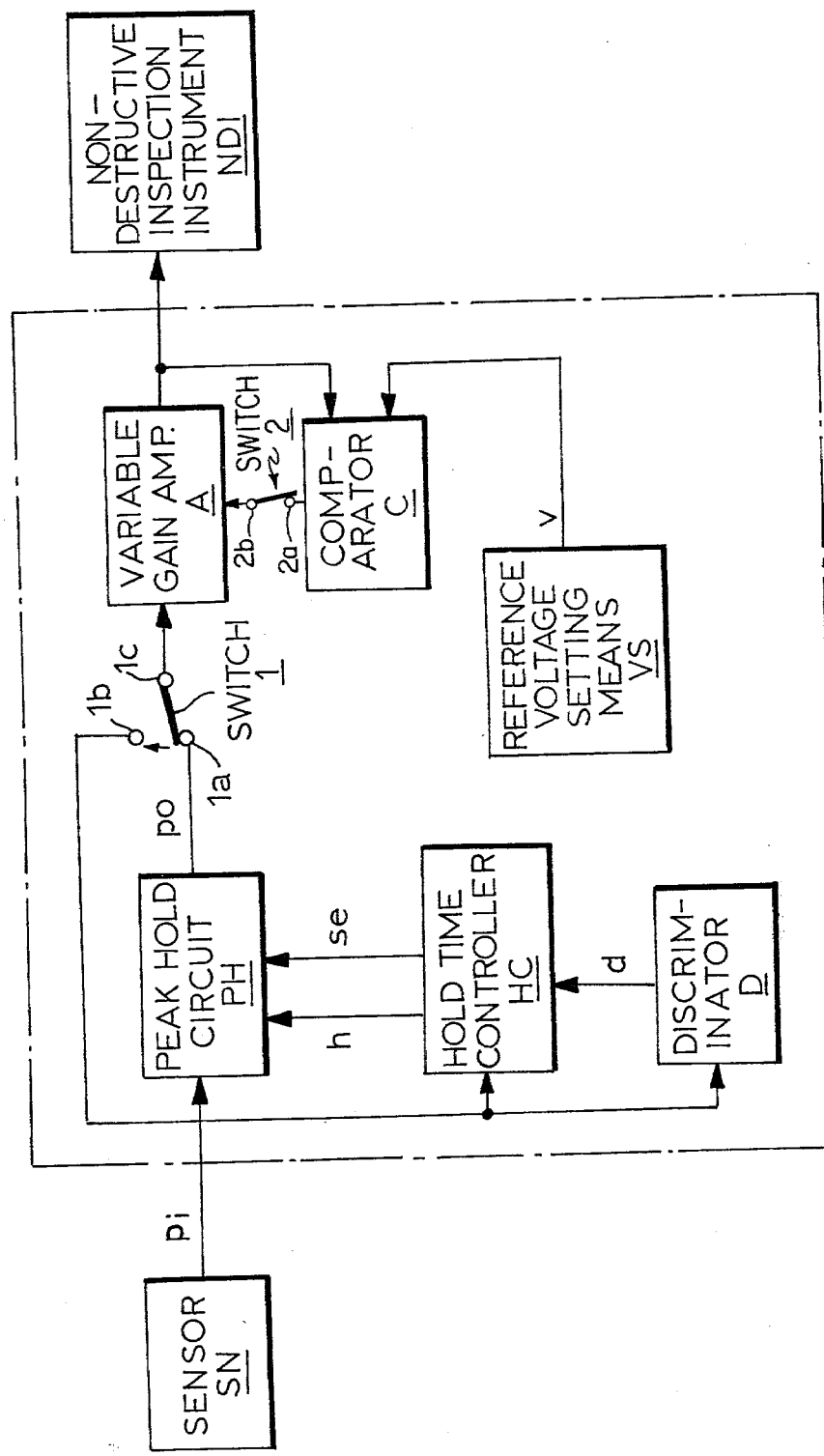
FIG. 1 is a block diagram for the apparatus of this invention.

Referring to FIG. 1 which illustrates an automatic sensitivity adjustment apparatus in broken dotted lines, PH stands for the peak hold circuit and D for the discriminator.

Both the peak hold circuit PH and the discriminator D are connected to a sensor SN of the nondestructive inspection instrument which generates an output pulse signal pi consisting of intermittently-appearing pulse waves, with a hold time controller HC being operatively interposed between the peak hold circuit PH and the discriminator D.

When a gate signal d from discriminator D reaches the input of the hold time controller HC, the latter circuit HC transmits a sampling enable signal to the peak hold circuit PH and, at the time when the peak value of the pulse signal pi is fed to the input of the peak hold circuit PH, transmits a hold signal h to the peak hold circuit PH.

Reference numeral 1 stands for a changeover switch, one of its terminals 1a being connected to the peak hold circuit PH and the other terminal 1b being connected to the sensor SN. The common terminal 1c of the switch 1 is connected to a variable gain amplifier A. Reference numeral 2 stands for a switch (break contact), one of its terminals 2a being connected to the output terminal of comparator C and the other terminal 2b being connected to the gain control terminal of the variable gain amplifier A. These switches enable the apparatus to be switched from a normal operation mode to an automatic calibration mode. The output terminal of the variable gain amplifier A is connected to the nondestructive inspection instrument NDI and the other input terminal of comparator C.

Figure 2:
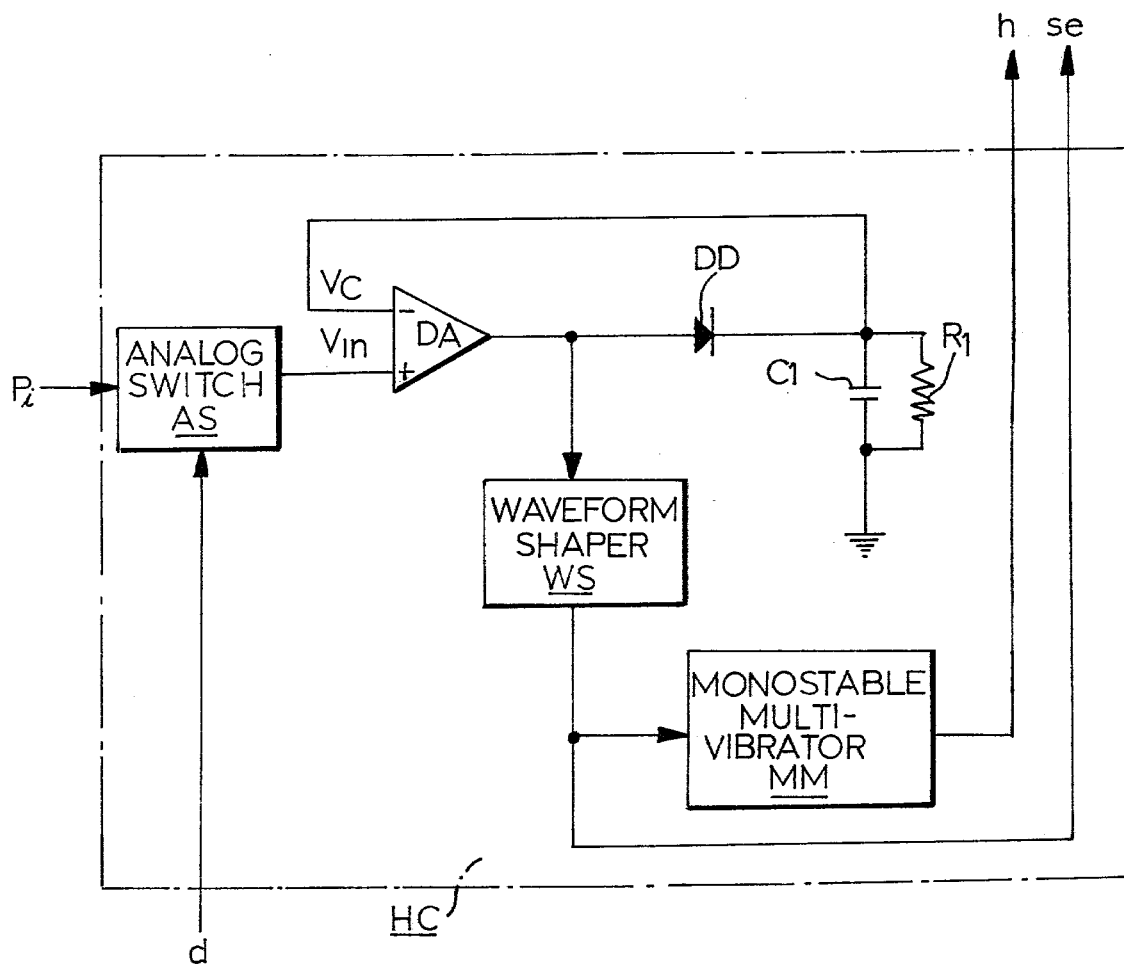
FIG. 2 is a block diagram partially in schematic form illustrating the details of the hold time controller.

The details of the structure of the hold time controller HC are illustrated in FIG. 2, while FIG. 3 illustrates the signals appearing at various points in the circuit of FIG. 2. Analog switch AS is controlled by the gate signal d. Analog switch AS is on during the gate signal d and thus converts pulse signal pi to Vin. Signal Vin is fed to the non-inverting input terminal of differential amplifier DA which has a large gain. The output signal Vo of differential amplifier DA is fed to the anode of diode DD and the input terminal of waveform shaper WS. The cathode of diode DD is connected to the inverting input terminal of differential amplifier DA and a parallel circuit having a capacitor Cl and a resistor R1. The output signal of wave shaper WS is directly transmitted to peak hold circuit PH and is fed to monostable multivibrator MM. This signal is the sampling enable signal se. The output signal of monostable multivibrator MM is the hold signal h, and this signal is transmitted to peak hold circuit PH.

The operation of hold time controller HC will now be described in conjunction with the waveforms illustrated in FIG. 3. As previously stated, discriminator D produces a gate signal d when the pulse signal pi exceeds a predetermined threshold level Ve. This gate signal d is used to control analog switch AS which has the pulse signal pi applied thereto. Since analog switch AS is "on" during gate signal d, analog switch AS produces an output Vin such as illustrated in FIG. 3(3). This signal Vin is applied to the non-inverting input of differential amplifier DA which is connected to form a modified voltage follower circuit. Because the gain of differential amplifier DA is large the output Vo of differential amplifier DA is driven to the voltage necessary to make the signal Vc applied to the inverting input of differential amplifier DA substantially equal to the signal Vin if this voltage is within the saturation limits of the differential amplifier DA. During the time Vin is increasing differential amplifier DA produces an output Vo which charges the capacitor C1 through diode DD to substantially the input voltage Vin. Thus as seen in FIGS. 3(3), 3(4) and 3(5) Vin, Vc and Vo are substantially equal during this period. After the peak value of pi is reached the signal Vin decreases to a value slightly less than the voltage Vc stored on capacitor C1. This causes the output Vo to decrease slightly. Diode DD prevents capacitor C1 from being discharged through the output of differential amplifier DA. Thus the signal Vc slowly decreases as illustrated in FIG. 3(4) as the charge stored on capacitor C1 is discharged through resistor R1. Because C1 and R1 are selected to have a decay time longer than the fall time of the signal pi, the output of differential amplifier DA decreases rapidly until it reaches the negative saturation level as illustrated in FIG. 3(5). Waveform shaper WS produces sampling enable signal se from signal Vo by limiting the signal to standardized voltage levels. Sampling enable signal se is applied to monostable multivibrator MM which produces hold signal h in the form of a short pulse at the trailing edge of sample enable signal se. It can be seen that sampling enable signal se begins when intermittant pulse signal pi exceeds the predetermined threshold level Vt of the discriminator D and ends when intermittent pulse signal pi reaches its peak value. Similarily, it can be seen that hold signal h occurs at the peak of intermittent pulse signal pi.

To operate the apparatus according to this invention thus far described, the discriminator D is previously set to a threshold voltage value Vt slightly lower than the anticipated peak value of the pulse signal pi generated by the sensor SN upon scanning of the control reference standard [FIG. 3(1)] while the reference voltage setting means VS is set to a voltage value V corresponding to the peak level of the nondestructive inspection instrument NDI which is considered to be optimal for display of the standard flaw in the reference standard.

If, the above arrangement, the changeover switch 1 is switched to the terminal 1a and the switch 2 is closed as illustrated placing the system in the automatic calibration mode and the sensor SN is caused to scan the control sample piece, the sensor Sn as it detects the standard flaw generates and transmits an intermittent pulse-wave, like the one shown in FIG. 3(1), to the peak hold circuit PH and discriminator D. Therefore, the gate signal d as shown in FIG. 3(2) is sent from the discriminator D to the hold time controller HC only while the voltage value of pulse signal pi is greater than the aforesaid threshold level Vt.

In the above situation, the hold time controller HC feeds a sampling enable signal se like the one shown in FIG. 3(6) to the peak hold circuit PH which, thereupon, starts sampling of the pulse-wave from the sensor SN. The hold time controller HC stops generating the sampling enable signal se at the moment when it detects the peak value of a pulse-wave contained in the intermittent pulse signal pi. At the same time, the hold time controller HC sends a hold signal h like the one shown in FIG. 3(7) to the peak hold circuit PH. As controlled by these signals of the hold control circuit HC, the peak hold circuit PH feeds an output signal po, like the one shown in FIG. 3(8), to the variable gain amplifier A through the switch 1, this output signal po being such that the peak value of the pulse-wave is sustained for a sufficient period of time.

The output signal of the variable gain amplifier A and the voltage V from the reference voltage setting means VS is fed to the comparator C and the resulting differential signal from comparator C is fed to the control terminal of the variable gain amplifier A. Since the variable gain amplifier A automatically varies its gain to adjust the aforesaid differential signal to zero, its output voltage assumes a constant value equal to the aforementioned set voltage V. The output signal po of the peak hold circuit PH drops somewhat at a time immediately after resetting as shown in FIG. 3(8) because output signal po follows intermittent pulse signal pi during sampling enable signal se. Therefore, if the switch 2 is opened during any time other than the above time period, the gain of the variable gain amplifier A will be fixed in such a manner that the peak value of the pulse-wave corresponding to the standard flaw will be properly displayed at the set voltage of the reference voltage setting means VS, i.e. the optimum peak level to be displayed on the nondestructive inspection instrument, thus enabling one to complete the necessary calibration of the nondestructive inspection instrument.

The scanning of an actual material for flaw detection purposed is accomplished with the apparatus of this invention whose gain has been thus fixed, by switching the changeover switch 1 to the 1b side to place the apparatus in the normal operation mode. In this way, the flaw signal for the test piece is fed from the sensor SN through switch 1 to the variable gain amplifier A with a fixed gain, thus enabling an accurate assessment of flaws in the test piece.

Thus, because the apparatus according to this invention is such that, in the calibration of nondestructive inspection instrument, the peak value of the pulse signal obtained by scanning a control reference standard is held for a predetermined time, it is sufficient that the scanning of the reference standard is performed only for a single standardized flaw.

Moreover, normally the only necessary procedure for calibration is to switch the changeover switch 1 and switch 2. Therefore, the desired calibration may be accomplished with great ease and in a short period of time. Furthermore, since the gain adjustment of the variable gain amplifier takes place automatically, there is obtained an exceedingly accurate calibration of the inspection instrument.

We claim:

1. An automatic sensitivity adjustment apparatus for use in calibration of a nondestructive inspection instrument having at least one sensor, said automatic sensitivity adjustement apparatus comprising:

a discriminator circuit connected to said sensor for producing a discrimination signal when the output of said sensor exceeds a predetermined level;

a peak hold circuit connected to said sensor having a sampling enable input and a hold input for sampling the output of said sensor upon receipt of a signal on said sampling enable input and for holding the sampled value upon receipt of a signal on said hold input;

a hold time controller connected to said discriminator circuit and to said peak hold circuit for detecting the peak of the output of said sensor, for providing a sampling enable signal to said peak hold circuit from the receipt of said discrimination signal until the detection of the peak of the output of said sensor and for providing a hold signal to said peak hold circuit upon detection of the peak of the output of said sensor;

a first switch means having a first terminal connected to said sensor, a second terminal coupled to the output of said peak hold circuit and a common terminal, for selectively coupling one of said first and second terminals to said common terminal under manual control;

a reference voltage setting means for producing a predetermined reference voltage;

a variable gain amplifier having an input coupled to said common terminal of said first switch means, an output terminal and a gain control terminal, for amplifying the signal applied to said input terminal by a factor dependent upon the signal applied to said gain control terminal;

a second switch means having a first terminal connected to said gain control terminal of said variable gain amplifier and a second terminal, for selectively coupling or decoupling said first and second terminals; and a comparator having a first input terminal coupled to said output terminal of said variable gain amplifier, a second input terminal coupled to said reference voltage setting means and an output terminal coupled to said second terminal of said second switch means, for producing an output signal which corresponds to the difference between the signal applied to said first input terminal and the signal applied to said second input terminal, whereby the gain of said variable gain amplifier is set so that the amplitude of the output of said variable gain amplifier equals the predetermined reference voltage when said first switch means couples the output of said peak hold circuit to said input of said variable gain amplifier and said second switch means couples the output of said comparator to the gain control terminal of said variable gain amplifier.

* * * * *